US006686146B2

(12) United States Patent
Deng et al.

(10) Patent No.: US 6,686,146 B2
(45) Date of Patent: *Feb. 3, 2004

(54) PROGNOSTIC METHODS FOR PREDICTION OF PROGRESSION OF NORMAL AND HYPERPLASTIC MAMMARY CELLS TO CARCINOMA

(75) Inventors: Guoren Deng, Walnut Creek, CA (US); You Lu, San Francisco, CA (US); Helene S. Smith, San Francisco, CA (US)

(73) Assignee: California Pacific Medical Center, San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 109 days.

(21) Appl. No.: 08/734,011

(22) Filed: Oct. 18, 1996

(65) Prior Publication Data

US 2002/0055096 A1 May 9, 2002

Related U.S. Application Data

(60) Provisional application No. 60/005,543, filed on Oct. 18, 1995.

(51) Int. Cl.[7] .......................... C12Q 1/68; G01N 33/58; G01N 33/60; C07H 21/00
(52) U.S. Cl. .............................. 435/6; 435/4; 436/501; 436/503; 436/504; 436/63; 436/64; 536/24.3; 536/24.31; 536/24.33; 536/23.1
(58) Field of Search .............................. 435/6, 7.23, 4; 436/63, 64, 501, 503, 504; 536/24.3, 24.31, 24.33, 23.1

(56) References Cited

PUBLICATIONS

Field et al. "Allele loss on chromosome 3 in squamous cel carcinoma of the head and neck correlates with poor clinical prognostic indicators" Int. J. Oncology. vol. 4 pp. 543–549, Mar. 4, 1994.*
Merriam Webster Online Dictionary, "adjacent", Nov. 11, 2001.*
Deng et al., Science 274: 2057–2059, Dec. 1996.*
Lydiate et al., The American Journal of Surgery (1944) 168:437–440.
Mitsudomi et al., Journal of the National Cancer Institute (1993) 85(24):2018–2023.
Deng et al., "Research on the loss of heterozygosity at different chromosome sites in patients with breast cancer" *Natl. Med. J. China* (*Zhonghua Yixue Zazhi*, 74(1):31–34 (Jan. 1994). English translation of Chinese text in item 3 of Suppl. IDS filed on Apr. 29, 1998.
Marchant, "Contemporary Management of Breast Cancer," *Obstetrics and Gynecology Clinics of North America* (1994) 21:555–560.
Colditz, "Epidemiology of Breast Cancer: Findings from the Nurses' Health Study," *Cancer Suppl.* (1993) 71:1480–1489.
Frykberg et al., "Management of In Situ and Minimally Invasive Breast Carcinoma," *W.J. Surg.* (1994) 18:45–57.
Adnane et al., "BEK and FLG, two receptors to members of the FGF family, are amplified in subsets of human breast cancers," *Oncogene* (1991) 6:659–663.
Posner et al., "Indications for Breast–Preserving Surgery and Adjuvant Therapy in Early Breast Cancer," *Int. Surg.* (1995) 79:43–47.
O'Connell, "Molecular Genetic Studies of Early Breast Cancer Evolution," *Breast Cancer Res. Treat.* (1994) 35:5–12.
Stratton et al., "Loss of Heterozygosity in Ductal Carcinoma In Situ of the Breast," *J.Pathol.* (1995) 175:195–201.
Koreth et al., "Mutation at Chromosome 11q23 in Human Non–Familial Breast Cancer: A Microdissection Microsatellite Analysis," *J.Pathol.* (1995) 176:11–18.
Tomlinson et al., "Loss of Heterozygosity on Chromosome 11q in Breast Cancer," *J. Clin. Pathol.* (1995) 48:424–428.
Zhuang et al., "Identical Allelic Loss on Chromosome 11q13 in Microdissected in Situ and Invasive Human Breast Cancer," *Cancer Res.* (1995) 55:467–471.
Tsuda et al., "Different Incidence of Loss of Heterozygosity on Chromosome 16q Between Intraductal Papilloma and Intracystic Papillary Carcinoma of the Breast," *Jpn. J. Cancer Res.* (1994) 85:992–996.
Chen et al., "Deletion of Two Separate Regions on Chromosome 3p in Breast Cancers," *Cancer Res.* (1994) 54:3021–3024.
Siegfried et al., "Loss of Heterozygosity on Chromosome 3p in Non–Small Cell Lung Carcinoma and Histologically Normal Lung Tissue Adjacent to Tumor," *Proc. Am. Assoc. Cancer Res.* (1995) 36:545 (Abstract, 3247).
Gilliland et al., "Clonality in Myeloproliferative Disorders: Analysis by Means of the Polymerase Chain Reaction," *Proc. Natl. Acad. Sci. USA* (1991) 88:6848–6852.
Fearon et al., "Clonal Analysis of Human Colorectal Tumors," *Science* (1987) 238:193–197.
Sidransky et al., "Clonal Origin of Bladder Cancer," *N. Eng. J. Med.* (1992) 326(11):737–740.
Jacobs et al., "Clonal Origin of Epithelial Ovarian Carcinoma: Analysis by Loss of Heterozygosity, p53 Mutation, and X–Chromosome Inactivation," *J. Natl. Cancer Inst.* (1992) 84:1793–1798.

(List continued on next page.)

Primary Examiner—Anthony C. Caputa
Assistant Examiner—Anne L. Holleran
(74) Attorney, Agent, or Firm—Morrison & Foerster LLP

(57) ABSTRACT

The present invention encompasses methods for determining the likelihood that benign hyperplastic breast tissue or normal breast tissue adjacent to carcinoma tissue will become malignant. The methods comprise substantially isolating the tissue; and determining loss of heterozygosity (LOH) at chromosome 3p24 in the tissue. LOH at chromosome 3p24 is a prognostic indicator that the tissue may become malignant.

14 Claims, 4 Drawing Sheets

OTHER PUBLICATIONS

Linder et al., "Distribution of Glucose–6–Phosphate Dehydrogenase Electrophoretic Variants in Different Tissues of Heterozygotes," *Am. J. Hum. Genet.* (1965) 17(3):212–220.

Gartler et al., "Glucose–6–Phosphate Dehydrogenase Mosaicism: Utilization in the Study of Hair Follicle Variegation," *Ann. Hum. Genet. London* (1971) 35:1–7.

Schmidt et al., "Development of the Pattern of Cell Renewal in the Crypt–Villus Unit of Chimaeric Mouse Small Intestine," *Devel.* (1988) 103:785–790.

Tsai et al., "Mosaicism in Human Epithelium: Macroscopic Monoclonal Patches Cover the Urothelium," *J. Urol.* (1995) 153:1697–1700.

Noguchi et al., "Discrimination Between Multicentric and Multifocal Carcinomas of the Breast Through Clonal Analysis," *Cancer* (1994) 74:872–877.

Anderson et al., "Risk of Familial Breast Cancer," *Cancer* (1985) 56:383–387.

Anderson et al., "Combined Effect of Family History and Reproductive Factors on Breast Cancer Risk," *Cancer* (1989) 63:349–353.

Hildreth et al., "The Risk of Breast Cancer After Irradiation of the Thymus in Infancy," *N. Engl. J. Med.* (1989) 321:1281–1284.

Miller et al., "Mortality From Breast Cancer After Irradiation During Fluoroscopic Examinations in Patients Being Treated for Tuberculosis," *N. Engl. J. Med.* (1989) 321:1285.

Modan et al., "Increased Risk of Breast Cancer After Low–Dose Irradiation," *Lancet* (1989) 1:629–630.

Tokunaga et al., "Breast Cancer Among Atomic Bomb Survivors," *Radiation Carcinogenesis Epidemiology and Biological Significance* (1984), Boice & Fraumeni (eds.) pp. 45–56, New York, Raven Press.

Spruck et al., "Distinct Pattern of p53 Mutations in Bladder Cancer: Relationship to Tobacco Usage," *Cancer Res.* (1993) 53:1162–1166.

Allen et al., "Methylation of Hpall and Hhal Sites Near the Polymorphic CAG Repeat in the Human Androgen–Receptor Gene Correlates with X Chromosome Inactivation," *Am. J. Hum. Genet.* (1992) 51:1229–1239.

Bergthorsson, J., et al., "Linkage analysis and allelic imbalance in human breast cancer kindreds using microsatellite markers from the short arm of chromosome 3" *Human Genetics* (1995) 96(4): 437–443.

Deng, G., et al., "Loss of heterozygosity and p53 gene mutations in breast cancer" *Cancer Res.* (1994) 54(2): 499–505.

Deng, G., et al., "Loss of heterozygosity at different chromosomes in patients with breast cancer" *National Med. J. China* (1994) 74(1): 31–34. (Partial English translation included).

Dahiya, R. and Guoren Deng, "Molecular prognostic markers in breast cancer" *Breast Cancer Research and Treatment*, 52:185–200 (1998).

Li, Zheng et al., "Increased Risk of Local Recurrence is Associated with Allelic Loss in Normal Lobules of Breast Cancer Patients" *Cancer Research*, 62:1000–1003 (2002).

* cited by examiner

A

B

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:1:

GTGCGCGAAG TGATCCAGAA                                              20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

TCTGGGACGC AACCTCTCTC                                              20

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:3:

AGAGGCCGCG AGCGCAGCAC CTC                                          23

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

GCTGTGAAGG TTGCTGTTCC TCAT                                         24

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

CATCTGAAAT GCTGACCTGT T                                            21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single (D) TOPOLOGY: linear (xi) SEQUENCE DESCRIPTION: SEQ ID NO:6:

AGCTGTCAGA ACTAAGTGCT T                                              21

(2) INFORMATION FOR SEQ ID NO:7:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:7:

AACGTTGGAC CTCAAGCCCA T                                              21

(2) INFORMATION FOR SEQ ID NO:8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:8:

AGAATGCCAA GGAAGGGTGC A                                              21

(2) INFORMATION FOR SEQ ID NO:9:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:9:

GTGCCCTTCC AGGAGTT                                                   17

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:10:

AGTGAGGCAT CCACTACC                                                  18

(2) INFORMATION FOR SEQ ID NO:11:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:11:

CAGCTGCCCT AGTCAGCAC                                                 19

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:12:

GCTTCCGAGT GCAGGTCACA                                        20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GATTTGAAAA TGAGCAGTCC                                        20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

GTCGGGCACT ACGTTTATCT                                        20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

AAGCAAATAT GCAAAATTGC                                        20

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:16:

TCCTTCTGTT TCTTGACTTA ACA                                    23

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CAATGGATGA TTTGATGCTG                                        20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued

```
       (xi) SEQUENCE DESCRIPTION: SEQ ID NO:18:

TGGTAGGTTT TCTGGGAAGG                                                    20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:19:

AGGTCTGGTT TGCAACTGGG                                                    20

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:20:

GAGGTCAAAT AAGCAGCAGG                                                    20

(2) INFORMATION FOR SEQ ID NO:21:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:21:

TCAGAAGGAA GTAGGAAGGA CTCAG                                              25

(2) INFORMATION FOR SEQ ID NO:22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:22:

GAAGAGCCTC GGTTATGGGT ATACA                                              25
```

PROGNOSTIC METHODS FOR PREDICTION OF PROGRESSION OF NORMAL AND HYPERPLASTIC MAMMARY CELLS TO CARCINOMA

CROSS REFERENCE TO RELATED APPLICATIONS

This application claims priority to U.S. provisional application Ser. No. 60/005,543 filed Oct. 18, 1995.

This invention was funded in part with funds from SPORE grant IP59CA58207. The Government may have certain rights to this invention.

DESCRIPTION

1. Technical Field

This invention relates to prognostic methods for use in predicting the likelihood that a normal or hyperplastic mammary cell will progress to neoplasia. The methods enable oncologists to determine the degree of aggressiveness to be employed in treatment of breast cancer and benign, hyperplastic, breast conditions.

2. Background

Breast cancer is one of the most common cancers and is the third leading cause of death from cancers in the United States with an annual incidence of about 182,000 new cases and nearly 50,000 deaths. In the industrial world, approximately one in eight women can expect to develop breast cancer in her lifetime. The mortality rate for breast cancer has remained unchanged since 1930. It has increased an average of 0.2% per year, but decreased in women under 65 years of age by an average of 0.3% per year. Preliminary data suggest that breast cancer mortality is beginning to decrease, probably as a result of an increase in the diagnosis of localized cancer and carcinoma in situ. For review, see, Marchant (1994) Contemporary Management of Breast Disease II: Breast Cancer, in: *Obstetrics and Gynecology Clinics of North America* 21:555–560; and Colditz (1993) *Cancer Suppl.* 71:1480–1489.

Although the etiology of breast cancer has not been elucidated, it is hypothesized to evolve from normal epithelium through certain nonmalignant proliferative diseases to carcinoma in situ, either ductal or lobule, to primary invasive cancer and finally, to metastatic cancer. At some point in the progression from normal tissue to malignancy, tumor initiation occurs. Tumor initiation and the early stages of progression, do not necessarily render a cell malignant, in fact, the cell may appear histologically normal. To date, there has been no method of detecting mammary cells which have undergone tumor initiation but which are not yet neoplastic.

The earliest and most favorable form of breast carcinoma capable of being recognized is the intraepithelial, or noninvasive, stage. Its early detection has been greatly increased by mammography. In situ carcinoma is characterized by a malignant transformation of the epithelial cells that line the breast lobules and major lactiferous ducts but without invasion of these malignant cells beyond the investing basement membrane into the surrounding stroma. For review, see Frykberg et al. (1994) *W. J. Surg.* 18:45–57.

Several genetic markers have been associated with breast cancer. A particular mutation in one of these, BRCA1, has recently been found to be associated with a specific ethnic group, Ashkenazi Jews, which has a particularly high incidence of breast cancer. A number of other tumor markers are associated with breast cancer, such as myc, p53, erbB2, bek, and flg. Adnane et al. (1991) *Oncogene* 6:659–661. The erbB2 gene (also known as HER-2/neu) encodes a 185 kDa membrane growth factor homologous to the epidermal growth factor receptor. The erbB2 gene is amplified in 61 of 283 tumors (22%) tested in a recent survey. Adnane et al. (1991).

Although original therapy for breast cancer was restricted to radical mastectomy, more conservative, breast-preserving, surgeries are now often available. Also, a wide variety of adjuvant therapies are now available including hormonal, radiation and chemotherapeutics. For review, see Posner et al. (1995) *Int. Surg.* 79:43–47. The availability of less radical treatment regimens necessitates methods of identifying patients who are destined to develop tumor recurrence. Although several promising prognostic factors have been identified, such as DNA ploidy, S-phase analysis, Cathepsin D, erbB2 oncogene expression and epidermal growth factor expression, designing treatment regimens based on these factors is thought to be "immature." Posner et al. (1995).

Another marker of cancer, particularly invasive breast cancer, is loss of heterozygosity (LOH). For review, see O'Connell (1994) *Breast Cancer Res. Treat.* 32:5–12. A particular LOH has been shown to be positively correlated with the change from in situ to invasive behavior. Stratton et al. (1995) *J. Pathol.* 175:195–201. In breast cancer, LOH has been shown at a variety of alleles. A high incidence of LOH has been found at chromosome 11q23 in non-familial breast cancers in situ, invasive and metastatic tumor cells. Koreth et al. (1995). *J. Pathol.* 176:11–18; and Tomlinson et al. (1995) *J. Clin. Pathol.* 48:424–428. LOH has been found, on chromosome 11q13 in 67% of microdissected invasive breast cancer and in a subpopulation of the in situ carcinomas of the invasive breast cancer. Zhuang et al. (1995) *Cancer Res.* 55:467–471. LOH has been found on chromosome 16q in intracystic papillary carcinomas in breast cancer and is thought to be involved in acquisition of malignant phenotype. Tsuda et al. (1994) *Jpn. J. Cancer Res.* 85:992–996. LOH has also been detected on two separate regions on chromosome 3p in breast cancers; 3p13–14 and 3p24–26. Chen et al. (1994) *Cancer Res.* 54:3021–3024.

There is circumstantial evidence in the literature that some breast cancers may result from multiple pathways within a localized region of the breast. Recently, invasive cancers and associated preinvasive and premalignant components such as ductal carcinoma in situ (DCIS) and atypical hyperplasia were examined for LOH at various autosomal loci. There were some cases which showed patterns of LOH consistent with the conclusion that the premalignant and invasive components resulted from two independent pathways of malignant progression. O'Connell et al. (1994)

LOH has also been found in a wide variety of tumors. In only one instance has a particular LOH, 3p21.3, been found in a tumor, non-small cell lung carcinoma, and in normal, adjacent, tissue. Siegfried et al. (1995) *Proc. Am. Assoc. Cancer Res.* 36:545 (Abstract, 3247).

All references cited herein, both supra and infra, are hereby incorporated herein by reference.

DISCLOSURE OF THE INVENTION

The present invention encompasses methods for determining the likelihood of benign hyperplastic breast tissue or normal breast tissue adjacent to carcinoma tissue will become malignant. The methods comprise substantially isolating the tissue; and determining the presence of loss of heterozygosity (LOH) at chromosome 3p24. LOH at chromosome 3p24 is a prognostic indicator that the tissue is likely to become malignant.

BRIEF DESCRIPTION OF THE DRAWINGS

FIGS. 1A and 1B are discussed in Example 1.

FIG. 2A depicts the histological section prior to microdissection. FIG. 2B depicts the slide after removal of the stromal tissue. FIG. 2C depicts the slide after removal of the normal cells.

FIG. 4A depicts the DNA from sample H21. In FIG. 4A, the top DNA band represents one allele and two lower molecular weight band. Lane 1 is the LOH from skin, lane 2 is the LOH from distal normal tissue, lanes 3–6 are four different areas of adjacent normal tissue, lane 7 is DCIS and lane 8 is invasive carcinoma. FIG. 4B depicts an autoradiograph of sample H12. In FIG. 4B, lane 1 is LOH from skin, lane 2 is adjacent normal, lane 3 is DCIS and lane 4 is invasive carcinoma.

MODES FOR CARRYING OUT THE INVENTION

Figure 1:
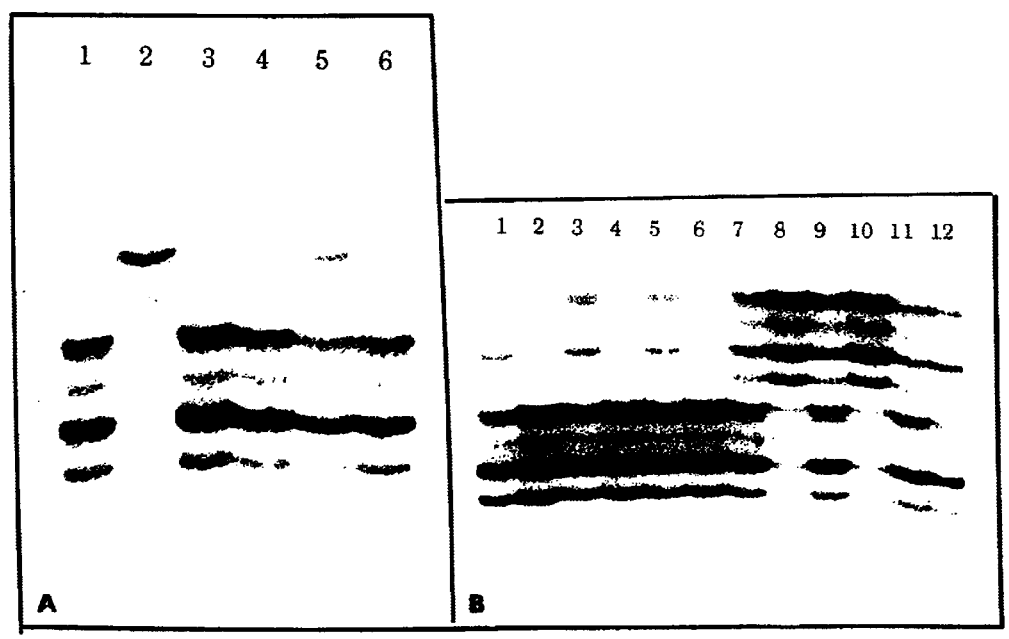
FIGS. 1A and 1B are a series of electrophoresis patterns depicting the X-chromosome inactivation pattern of the androgen receptor gene in normal human epithelium.

Analysis of X-chromosome inactivation has been used to determine the clonality of several kinds of tumors in female patients including leukemias, colorectal, bladder and ovarian tumors. Gilliland et al. (1991) *Proc. Natl. Acad. Sci. USA* 88:6848–6852; Fearon et al. (1987) *Science* 238:193–197; Sidransky et al. (1992) *N. Engl. J. Med.* 326:737–740; and Jacobs et al. (1992) *J. Natl. Cancer Inst.* 84:1793–1798. These studies rely on the fact that X-chromosome inactivation occurs at the preimplantation stage of development resulting in the permanent marking of cellular progeny by random inactivation of either the paternal or maternal X-chromosome. Tissue clonality can be assessed by analyzing the methylation status of polymorphic DNA markers on X-linked genes, since extensive de novo methylation is associated with their permanent inactivation.

While several of the above studies have shown that tumors are clonal, less attention has been paid to the composition of normal tissues from the standpoint of clonality. Early studies showed the existence of large patches of monoclonal normal cells ranging in size from 0.2 to 1.0 mm$^2$ in the hair follicles, gastric epithelium and female bladder urothelium. Linder et al. (1965) *Am. J. Hum. Genet.* 17:212–220; Gartler et al. (1971) *Ann. Hum. Genet. London* 35:1–7; Schmidt et al. (1988) *Devel.* 103:785–790; and Tsai et al. (1995) *J. Urol.* 153:1697–1700. In a previous study of X-chromosome inactivation in the human breast, it was concluded that normal breast tissue was polyclonal in origin with random distribution of cells having either allele on the X-chromosome hypermethylated and hence inactivated. Noguchi et al. (1994) *Cancer* 74:872–877.

Results which indicate that premalignant and invasive components arise from independent pathways present a dilemma; why does more than one presumably rare event leading to malignant progression occur at the same time in a localized region of the breast? If the patient had inherited a mutated causal gene, one would expect multicentric disease to occur anywhere in either breast. In fact, bilaterality is a characteristic of familial breast cancer. Anderson et al. (1985) *Cancer* 56:383–387; and Anderson et al. (1989) *Cancer* 63:349–353. The usual model of malignant progression suggests that proliferation of an initiated cell provides the target population for acquisition of subsequent progression-related mutations. If, however, a stem cell has undergone tumor initiation prior to mammary gland differentiation, when subsequent hormonal changes induce extensive proliferation of the mammary tree, the initiated cell could populate a single localized region of the breast. This region (where all cells would have the same inactivated X-chromosome) would be at an increased cancer risk.

If tumor initiation occurs prior to mammary gland differentiation, this would increase the target cell population, theoretically resulting in an increased incidence of breast cancer in the adult. Extensive epidemiologic evidence for increased breast cancer incidence with radiation as the initiating agent supports this hypothesis. Hildreth et al. (1989) *N. Engl. J. Med.* 321:1281; Miller et al. (1989) *N. Engl. J. Med.* 321:1285; Modan et al. (1989) *Lancet* 1:629, and Tokunaga et al. (1984) in *Radiation Carcinogenesis Epidemiology and Biological Significance,* Boice & Fraumeni (eds.) pp. 45–46, New York, Raven Press. The highest increase in breast cancer risk was seen in individuals younger than age 14 who had been treated with multiple fluoroscopies for the management of pulmonary tuberculosis and in women who were in the first decade of life at the time of exposure to atomic bomb irradiation. Tokunaga et al. (1984).

X-chromosome inactivation was applied to understanding human breast morphogenesis by examining ducts and lobules of normal breast tissue. Since epithelium was not specifically isolated, in the studies performed by Noguchi et al. (1994), the microdissected normal breast tissue used in the previous study contained both stromal and epithelial components. Mammary epithelium and stroma might have arisen from different stem cells, the examples provided herein describe the results of a reevaluation of the clonality of normal breast epithelium.

The data presented herein establish that mammary epithelium in the human breast is organized into discrete regions in which all cells have the same inactive X-chromosome. Hence, multiple tumors could arise from initiated cells independently progressing to malignancy within a circumscribed cellular patch containing the same inactive X-chromosome. Thus, inactivation of a single X chromosome in a tumor may indicate a clonal origin for the tumor, but does not address the question of clonal progression.

We undertook a study of LOH at chromosome 3p24 known to be frequently seen in invasive breast cancer. As a comparison, we also measured the presence of LOH at three other loci, chromosomes 11p15.5, 13q13 and 17p13.1 (p53 gene), where LOH is also frequently detected in invasive breast cancer. DNA from invasive carcinoma, ductal carcinoma in situ (DCIS) and normal lobule adjacent to tumors was tested for LOH at these four loci. No case was seen with LOH at 13q13 in adjacent normal lobules. For 11p15.5 and 17p13.1, there was one case of 16 informative cases and one of 19 informative cases respectively, where the adjacent normal lobules contained LOH. The most surprising result was that there was relatively frequent LOH at 3p24 in the adjacent normal lobules, LOH was detected in 6 of 17 informative cases (35%). Further, the 3p24 LOH in adjacent normal tissue was relatively discrete in that it did not extend to 3p22. Thus, LOH may increase as tumor progression continues. This finding indicated that LOH at 3p24 is an early event for breast cancer initiation. Thus, LOH at this locus is useful as a marker for early diagnosis, prognosis, or for the cloning of a gene or genes involved in breast cancer initiation.

Thus, the invention encompasses methods for determining the likelihood of various target tissues such as benign and normal breast tissues of progressing to carcinoma in situ and finally invasive carcinoma. Benign tissues are usually characterized as hyperplastic and are often termed cysts or proliferative disease without atypia. The normal breast tissue includes that adjacent to carcinoma tissue. Given the results presented herein which indicate that the epithelia of breast tissue can be clonal, there is a likelihood that tissue adjacent to a carcinoma is derived from the same stem cell as the carcinoma and thus may have undergone the initiating events leading to carcinoma. This is true despite an otherwise normal histological profile of the adjacent tissue. Thus the adjacent tissue is that epithelial tissue immediately adjacent to the carcinoma cells.

The methods encompass determining the LOH at chromosome 3p24 in the target tissues. LOH can be measured by any method known in the art. Preferably, the methods described herein are used. LOH analysis is performed on substantially isolated tissue. In the case of benign hyperplastic tissue it is readily isolated from adjacent normal tissue. Care should be taken in all cases to isolate the epithelial tissue from the surrounding stromal tissue. In the case of normal tissue adjacent to carcinoma tissue, microdissection techniques, such as those described herein, are preferred. The carcinoma tissue can be any breast carcinoma including, but not limited to, interstitial in situ carcinoma, ductal in situ carcinoma and invasive carcinoma.

Should LOH at chromosome 3p24 be found in the target tissue, more aggressive treatment regimens may be performed. For instance, larger resection or mastectomy may be performed and adjuvant chemotherapy may be given.

The following examples are meant to illustrate, but not limit, the claimed invention.

EXAMPLE 1

X-Chromosome Inactivation in Breast Tissue

Single normal lobules or large ducts were carefully microdissected from individual hematoxylin-eosin stained 4 micron sections from nonmalignant breast epithelium from 2 reduction mammaplasties and a mastectomy. Microdissection was performed essentially as described by Spruck et al. (1993) Cancer Res. 53:1162–1166 as modified by Tsai et al. (1995). Briefly, a single normal duct was microdissected with a surgical scalpel from a hematoxylin-eosin stained slide (standard 4 micron section) using 100 fold magnification. After carefully scraping away surrounding stroma, the isolated duct was picked up using a new blade and transferred to an Eppendorf tube. The same histological areas from 4 sequential slides were microdissected and pooled to obtain sufficient cells for an X-chromosome inactivation study. The DNA was extracted with proteinase K according to the method described by Allen et al. (1992) Am. J. Hum. Genet. 51:1229–1239 except that the boiling steps were omitted to maintain the DNA in double stranded form for subsequent enzymatic analysis. Proteinase K activity was inhibited with 1 mM final concentration of phenylmethylsulfonyl fluoride (PMSF).

Exon 1 of the human androgen receptor gene has three HhaI and two HpaII restriction endonuclease sites within 100 bp 5' to a polymorphic CAG repeat region. The CAG repeat polymorphisms were used to distinguish between the two X-chromosome alleles in informative females. Since methylation of the HhaI and HpaII restriction endonuclease sites was associated with lack of gene expression on the inactive X-chromosome (Allen et al. (1992)), cleavage with the methylation sensitive restriction endonucleases HhaI and HpaII, was used to distinguish between the active and inactive gene. Prior to PCR amplification, DNA was digested with HhaI and HpaII. This restriction endonuclease digestion caused the restriction sites on the unmethylated active X-chromosome to be cleaved whereas the sites on the inactive X-chromosome remained intact.

After digestion, samples were amplified by two PCR reactions using nested primers specific for exon 1 of the androgen receptor-gene. The two sets of oligonucleotide primers were designed to flank both of the methylation-sensitive restriction enzyme sites together with the CAG repeat. Therefore, PCR amplification yielded a product only from the uncleaved (inactive) X-chromosome. Therefore only one band was present in the gel. In contrast, PCR amplification of DNA extracted from cells where either allele was randomly inactivated (or PCR amplification of an undigested DNA control) yielded products from both the active and inactive X-chromosome.

X-inactivation analysis using the above scheme was performed according to the method described by Jacobs et al. (1992). Briefly, the DNA solution from each microdissected region was divided into two aliquots and subjected to either double digestion at 1–2 units each of HhaI and HpaII or mock digestion with the restriction enzyme buffer provided by the manufacturer and incubated for 90 min. at 37° C. The primary PCR was performed with outside primers 1A and 1B (1A:5'-GTGCGCGAAGTGATCCAGAA(SEQ ID NO:1)-31'; and 1B: 5'-TCTGGGACGCAACCTCTCTC (SEQ ID NO:2)-3') in a standard reaction volume of 25 $\mu$l and consisted of 17 cycles at 94° C. for 1 min., 55° C. for 1 min., and 72° C. for 1.5 min. The secondary PCR was performed with inside primers 2A and 2B (2A, 5'-AGAGGCCGCGAGCGCAGCACCTC(SEQ ID NO:3)-3'; and 2B, 5'-GCTGTGAAGGTTGCTGTTCCTCAT(SEQ ID NO:4)-3'), 0.8 $\mu$l to 1.0 $\mu$l of the primary PCR product as the template, 2 $\mu$Ci of [$\alpha$-$^{32}$P]dCTP, and consisted of 28 cycles at 94° C. for 1 min., 66° C. for 1 min., and 72° C. for 1.5 min. For both PCR reactions, the initial denaturation and final elongation steps were lengthened to 2 min. and 3 min., respectively. The radioactively labeled secondary PCR products were analyzed by electrophoresis on a 5% denaturing polyacrylamide gel and subjected to autoradiography. The results obtained are depicted in FIG. 1. In FIG. 1, odd numbered lanes illustrate mock digested controls, even numbered lanes illustrate samples digested with HhaI/HpaII. FIG. 1A represents the results obtained from the reduction mammaplasty case 1 where all three lobules were distinct and on the same section; lanes 1 and 2 were from lobule 1, lanes 3 and 4 were from lobule 2, and lanes 5 and 6 were from lobule 3. FIG. 1B represents the results obtained from the reduction mammaplasty case 2 where lobules 1 to 3 were on one section and lobules 4 to 6 were on one section from a different block; lanes 1 and 2 are from lobule 1, lanes 3 and 4 were from duct 2, lanes 5 and 6 were from lobule 3, lanes 7 and 8 were from lobule 4, lanes 9 and 10 were from lobule 5 and lanes 11 and 12 were from lobule 6.

The size of the microdissected regions ranged from 0.08 to 0.45 mm$^2$. In the mammary gland, the patches with a single inactivated X-chromosome could also be significantly larger since, in one reduction mammaplasty (case 2) and in the peripheral mastectomy tissue (case 3), only one hypermethylated allele in all of the dissected regions within a tissue block was found. These results are presented in Table 1. Multiple blocks representing different regions of the breast were available for case 2 and they differed in inactivated allele. Some of the microdissected regions showed equal retention of each allele (FIG. 1b, lanes 11 and 12 and Table 1) suggesting that some ducts and/or lobules may be polyclonal or that contaminating stroma contributed to the polyclonal pattern.

TABLE 1

Clonality of Mammary Tissue Determined by X-Chromosome Inactivation

| Source of Tissue (case) | Tissue Block | Type of Mammary Tissue | Androgen Receptor Allele Lost After Digestion[1] | Size of Dissected Area (mm$^2$) |
|---|---|---|---|---|
| Reduction Mammaplasty (Case 1) | A | lobule (1)[2] | bottom | 0.33 |
|  | A | lobule (2) | top | 0.45 |
|  | A | lobule (3) | top | 0.30 |
| Reduction Mammaplasty (Case 2) | A | lobule (1) | top | 0.30 |
|  | A | duct (2) | top | 0.27 |
|  | A | lobule (3) | top | 0.21 |
|  | B | lobule (4) | bottom | 0.11 |
|  | B | lobule (5) | bottom | 0.17 |
|  | B | lobule (6) | neither | 0.08 |
|  | C | ducts | neither | 0.08 |
|  | D | ducts | neither | 0.12 |
|  | E | lobule | neither | 0.12 |
| Peripheral Mastectomy (Case 3) | A | lobule | top | 0.55 |
|  | A | lobule | top | 0.48 |
|  | A | lobule | top | 0.50 |

[1]Digestion with methylation sensitive enzymes
[2]Number in parentheses refers to illustration in Figure 1

The results depicted in FIGS. 1A and 1B and Table 1 indicate that in both normal reduction mammaplasties tested and in the nonmalignant breast tissue peripheral to a carcinoma, discrete patches of cells with a single inactivated X-chromosome were detected. In FIG. 1, each allele is represented by a main band and several weaker bands. These weaker bands arise during PCR due to slippage of the DNA strand being synthesized along its template with a CAG repeat.

EXAMPLE 2

Loss of Heterozygosity on the Short Arm of Chromosome 3

Understanding the genetic aberrations of these changes, especially those associated with the tumor initiation (early event) will contribute to the early diagnosis of breast cancer, treatment of the patients, and the effective management of the high-risk population. LOH is an event to unmask a mutant allele of a gene which may play a role in suppressing the tumor formation (tumor suppressor gene). Thus, LOH is considered an important marker for tumor initiation or progression. Tumor initiation is hypothesized to occur prior to mammary gland differentiation. If this is the case, one may be able to find genetic changes associated with early stages of carcinoma in morphologically normal mammary lobules adjacent to carcinoma. As shown above, breast tissue may be clonal in nature, with different duct and lobule systems arising from different stem cells. The results presented below indicate that LOH on the short arm of chromosome 3 was detected frequently in the normal epithelium adjacent to breast cancer. This finding supports the breast tumor initiation theory.

Figure 2:
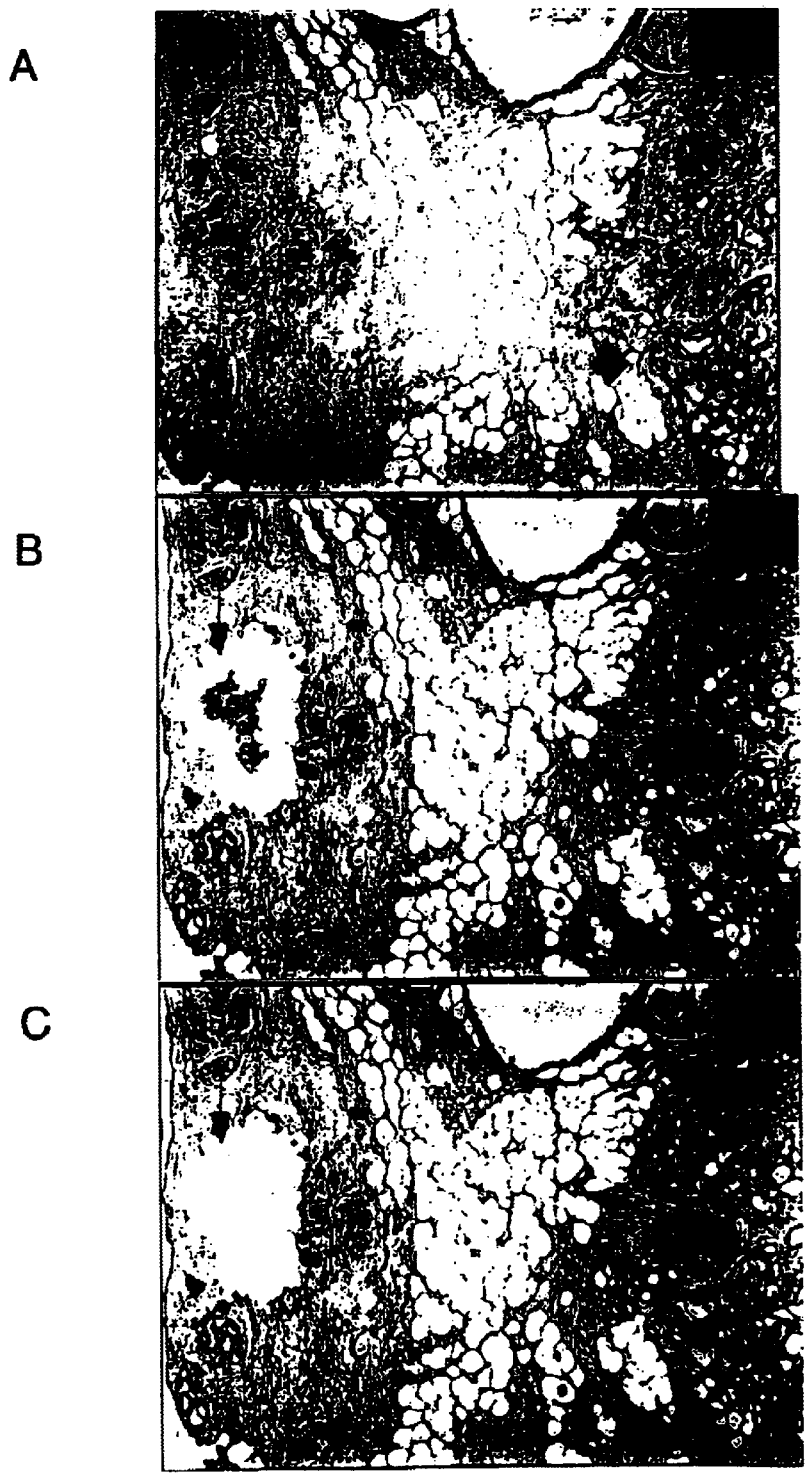
FIGS. 2A, 2B and 2C are a series of photomicrographs depicting the microdissection of adjacent normal cells from tissue sections.

The selected areas of normal lobules, DCIS and invasive tumor were microdissected from individual hemratoxylin-eosin stained, 4 micron thick section under light microscope. Essentially, the microdissection was performed as described in Example 1. FIG. 2 depicts the steps of the microdissection technique. After carefully scraping away the surrounding tissue with a surgical scalpel, the isolated area was picked up using a new blade and transferred to an Eppendorf tube. DNA was isolated from the microdissected tissues according to the following procedure. Tissue was extracted with 100 μl of xylenes (Fisher reagent grade) to remove the paraffin and treated with 100 μl of 95% ethanol. After air-drying, the tissue pellet was digested in 20–50 μl of solution containing 0.1 M Tris-HCl, pH 8, 1 mM EDTA, 0.50%. Tween 20(Fisher) and 0.1 mg/ml proteinase K at 50° C. overnight. The digestion mixture was heated at 95° C. for 5 min. to inactivate the proteinase K, diluted to 100–500 μl with a buffer comprising 10 mM Tris-HCl, pH 8, 1 mM EDTA buffer and stored at −20° C. until use.

The DNA samples were then amplified by polymerase chain reaction (PCR) with polymorphic primers located at chromosomes 3p24, 11p15.5, 13q13 and 17p13.1 (Table 2). PCR was performed according to the following procedure: 4 μl of DNA was amplified by PCR in 50 μl of a solution containing 10 mM Tris-HCl, pH 8.3, 50 mM KCl, 2 mM MgCl$_2$, 0.01% gelatin, 200 μM each of dATP, dGTP, dCTP and dTTP, 0.1 μM upstream and downstream primers, 1% DMSO, 0.44 μg Taq antibody (Clontech) and 2 units of Taq polymerase. PCR was processed for 45 cycles of denature (94° C. for 1 min.), annealing (56–66° C. for 1 min.) and chain extension (72° C. for 1 min.). The annealing temperature for each pair of primers was listed in Table 2. After PCR, 5 μl of the PCR product was digested with the restriction endonuclease indicated in Table 2, and the digested fragments were separated on a 4% polyacrylamide gel. For some of the microsatellite polymorphic loci (non-RFLP) (including CA repeat and tetranucleotide), PCR was performed as above except 1 μCi [α-$^{32}$p] dCTP was added to the reaction mixture, and the concentration of 4 deoxyribonucleotide triphosphates was reduced to 20 μM. 1 μl of the PCR product was mixed with 3 μl of sequencing stop solution (United States Biochemicals), denatured by heating and electrophoresed on a 6% sequencing gel. Each allele of the PCR product was measured by reading the optical density with a densitometer after photographing the ethidium bromide-stained gel with negative film or after exposing the X ray film to the gel. The ratios of the two alleles (the undigested allele over the digested, or the top allele over the bottom) for different tissues were counted. The results are presented in Table 2. In Table 2, RE stands for restriction endonuclease, the DNA sequences are represented 5' to 3' and RFLP stands for restriction fragment length polymorphism. The invasive tumor, DCIS or normal lobule samples in which the ratios of the two alleles relative to that for the normal skin show greater than 30% alteration were considered as LOH.

Figure 4:
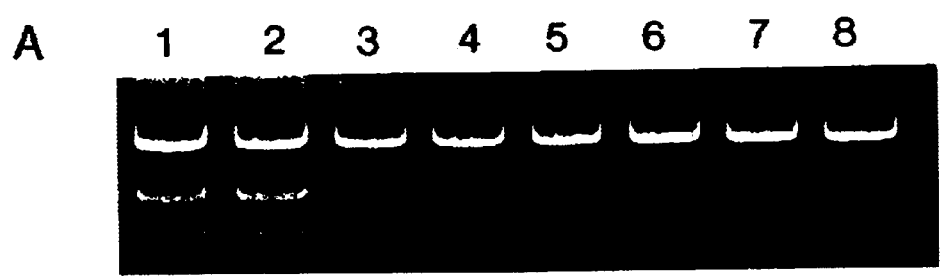
FIGS. 4A and 4B depict the LOH assay of PCR products.
Figure 4:

FIG. 4 depicts the LOH at locus 3p24 in normal lobule, DCIS and invasive tumor of sample H21(A) and H12(B). Note that in FIG. 4A, skin and distal normal tissue are heterozygous at chromosome 3p24 (three bands on gel) whereas four different areas of adjacent normal tissue, DCIS and invasive carcinoma all show LOH at chromosome 3p24 (only one band on gel). In FIG. 4B, the difference in density of the upper band in adjacent normal, DCIS and invasive carcinoma compared to skin indicates LOH in the test samples.

TABLE 2

Sequences of Primers Used for LOH Analysis

| Name | Locus | Sequence | Ann. temp. | Size of product (bp) | Polym. type | RE |
|---|---|---|---|---|---|---|
| EABH3 (SEQ ID NO:5) | 3p24 | CATCTGAAATGCTGACCTGTT | 60° C. | 208 | RFLP | HindI |
| EABH4 (SEQ ID NO:6) | | AGCTGTCAGAACTAAGTGCTT | | | | II |
| EABMD1 (SEQ ID NO:7) | 3p24 | AACGTTGGACCTCAAGCCCAT | 60° C. | 210 | RFLP | MspI |
| EABMD4 (SEQ ID NO:8) | | AGAATGCCAAGGAAGGGTGCA | | | | |
| D3S1244F (SEQ ID NO:9) | 3p24 | GTGCCCTTCCAGGAGTT | 56° C. | 177–189 | tetra-nucleotide | |
| D3S1244R (SEQ ID NO:10) | | AGTGAGGCATCCACTACC | | | | |
| TH2.1 (SEQ ID NO:11) | 11p15.5 | CAGCTGCCCTAGTCAGCAC | 66° C. | 244–260 | tetra-nucleotide | |
| TH2.2 (SEQ ID NO:12) | | GCTTCCGAGTGCAGGTCACA | | | | |
| D13S218F SEQ ID NO:13) | 13q13 | GATTTGAAAATGAGCAGTCC | 56° C. | 187–195 | CA | |
| D13S218R (SEQ ID NO:14) | | GTCGGGCACTACGTTTATCT | | | CA | |
| D13S219F (SEQ ID NO:15) | 13q13 | AAGCAAATATGCAAAATTGC | 56° C. | 117–127 | CA | |
| D13S219R (SEQ ID NO:16) | | TCCTTCTGTTTCTTGACTTAACA | | | CA | |
| TP53.5.1 (SEQ ID NO:17) | 17p13.1 | CAATGGATGATTTGATGCTG | 60° C. | 196 | RFLP | BstUI |
| TP53.5.2 (SEQ ID NO:18) | | TGGTAGGTTTTCTGGGAAGG | | | | |
| TP53.6.1 (SEQ ID NO:19) | 17p13.1 | AGGTCTGGTTTGCAACTGGG | 60° C. | 107 | RFLP | MspI |
| TP53.6.2 (SEQ ID NO:20) | | GAGGTCAAATAAGCAGCAGG | | | | |
| TP53.8.1 (SEQ ID NO:21) | 17p13.1 | TCAGAAGGAAGTAGGAAGGACTCAG | 60° C. | 90 | RFLP | BamHI |
| TP53.8.2 (SEQ ID NO:22) | | GAAGAGCCTCGGTTATGGGTATACA | | | | |

The incidence of LOH at four chromosome loci in various components of breast cancer are summarized in Table 3.

TABLE 3

Incidence of LOH in Various Components of Breast Cancer
No. with LOH/Total Informative Cases (%) at Components

| | 3p24 (%) | 11p15.5 (%) | 13q13 (%) | 17p13.1 (%) |
|---|---|---|---|---|
| Invasive | 10/21 (48) | 5/17 (29) | 10/14 (71) | 16/20 (80) |
| DCIS | 9/20 (45) | 2/18 (11) | 7/14 (50) | 14/20 (70) |
| Normal lobule | 6/17 (35) | 1/16 (6) | 0/11 (0) | 1/19 (5) |

To determine whether the LOH at 3p was a property of all the normal mammary epithelium or was seen only in the normal lobules adjacent to the carcinoma, the normal lobules from blocks taken distant to the carcinomas were evaluated. Of the 6 cases with LOH at 3p in the adjacent normal lobules, distant blocks were available for 4 of them. In all 4 cases, the distant lobules showed no LOH (Table 4). In one of these cases (H21), there was a complete LOH indicating that all of the lobular epithelium had the LOH. The other three cases showed only partial LOH. However, even the most careful dissection of normal lobules includes some contaminating stromal cells. Therefore, it is impossible to distinguish whether only some of the cells in the lobules had the LOH or whether the partial loss was due to contamination with stromal cells.

TABLE 4

LOH at 3p24 In Normal Mammary Lobules Adjacent to Carcinoma

| Case | Density Ratio of Upper Allele to Lower Allele DNA from Distant Normal Lobules | DNA from Adjacent Normal Lobules |
|---|---|---|
| H12 | 1.0/0.95 | 0.15/1.0 |
| H21 | 1.0/0.92 | 1.0/0.03 |
| H22 | 1.0/0.97 | 1.0/0.56 |
| H37 | 1.0/1.0 | 0.25/1.0 |

Subsequent to these experiments, a number of control experiments were undertaken to exclude potential artifacts. These artifacts were of two types:. 1) the technique was erratic and not reproducible, and 2) the normal lobules chosen for dissection actually contained cancer cells due to Pagetoid extension of the DCIS cells.

We undertook a number of experiments to evaluate reproducibility of the assay. Using the same DNA preparations, we repeated the assay several times (Table 5). There was some difference in the proportion of loss, particularly for the cases with only partial loss. However, in every assay when an LOH was recorded, the same allele was lost in each repeat assay in all cases. If the LOH were due to random artifacts of the assay methodology, one would expect to have either allele lost randomly in repeat experiments.

TABLE 5

Reproducibility of the PCR Assay for LOH

| Sample | Density ratio of upper allele to lower allele in adjacent lobules |
|---|---|
| H12 | 0.31/1.0 |
|  | 0.13/1.0 |
|  | 0.42/1.0 |
|  | 0.54/1.0 |
| H21 | 1.0/0.05 |
|  | 1.0/0.03 |
| H22 | 1.0/0.48 |
|  | 1.0/0.34 |
|  | 1.0/0.19 |
|  | 1.0/0.22 |
|  | 1.0/0.56 |
| H36 | 0.48/1.0 |
|  | 0.52/1.0 |
| H37 | 1.0/0.02 |
|  | 1.0/0.03 |
|  | 1.0/0.08 |
|  | 1.0/0.14 |
| H40 | 1.0/0.25 |
|  | 1.0/0.48 |
|  | 1.0/0.47 |
|  | 1.0/0.39 |

To exclude the possibility that the artifact related to the DNA preparation, one case was evaluated by dissecting 4 individual lobules and extracting the DNA separately. Again, in each adjacent lobule, the same allele was lost (Table 6 and FIG. 4).

TABLE 6

LOH at Chromosome 3p24 in Individual Normal Lobules Adjacent to a Breast Carcinoma

| Lobule | Density ratio of upper allele to lower allele in adjacent normal lobules |
|---|---|
| 1 | 1.0/0.05 |
| 2 | 1.0/0.10 |
| 3 | 1.0/0.05 |
| 4 | 1.0/0.05 |

The second potential artifact, namely that the adjacent lobules contained cancerous cells was excluded by three approaches. First, photomicrographs of an adjacent section to the dissected lobules appeared to have completely normal histology. Secondly, in a number of cases, the DCIS and invasive components adjacent to the normal lobule had additional LOHs besides 3p24 which were not seen in the normal lobules (Table 7). For example, DNA from the normal adjacent lobules of case H12 (Table 7) showed an LOH at 3p24 but not at 17p13.1 even though both the DCIS and invasive components had LOH's at both loci. Table 7 also summarizes the cases where the normal lobules had a LOH at 11p15.5 and 17p13.1 respectively, again showing that the DNA from the normal cells differed from that of the DCIS and invasive cancers.

TABLE 7

LOH at Various Chromosomal Loci in Cases with Chromosomes 3p24 LOH In Adjacent Normal Lobules

| | 3p24 | | | 11p15.5 | | | 13q13 | | | 17p13.1 | | |
|---|---|---|---|---|---|---|---|---|---|---|---|---|
| Case | NA | DC | IN | NA | DC | IN | NA | DC | IN | NA | DC | IN |
| H12 | Y | Y | Y | N | N | Y |  |  |  | N | Y | Y |
| H21 | Y | Y | Y |  |  |  |  |  |  | N | Y | Y |
| H37 | Y | Y | Y |  |  |  |  |  | Y | N | Y | Y |
| H40 | Y | Y | Y | N | N | N | N | N | N | N | Y | Y |
| H5 |  |  |  | Y | Y | Y | N | Y | Y |  |  |  |
| H6 |  |  |  | N | N | N | N | Y | Y | Y | Y | Y |

Figure 3:
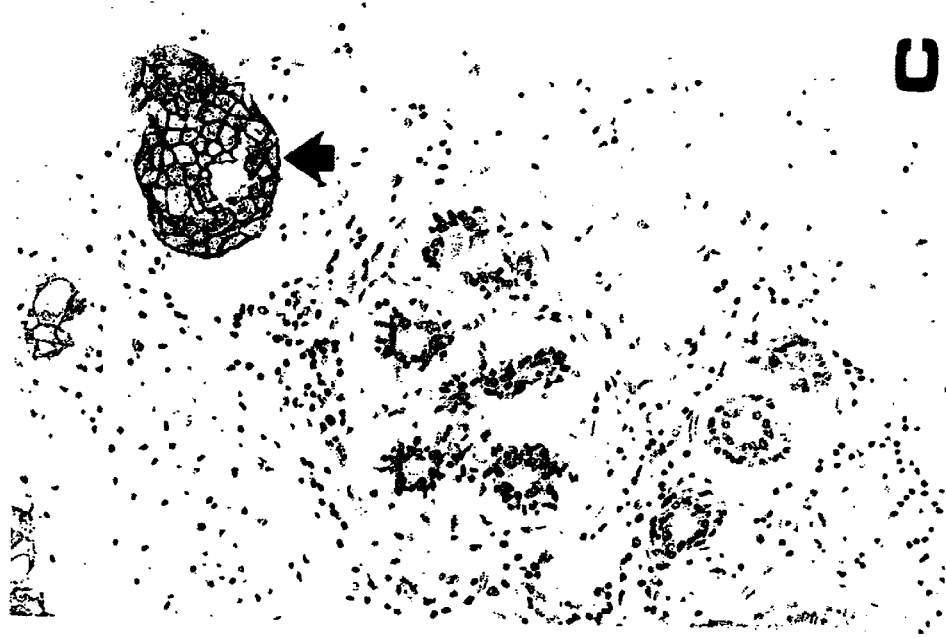
FIG. 3 is a photomicrograph depicting hematoxylin-eosin staining of erbB2 expressing breast cancer cells.

A third method used to exclude the possibility that the normal lobules contained tumor cells was by immunostaining with antibody to erbB-2 protein. In cases where the invasive tumor and the DCIS components each had a least 30% of the cells immunopositive for erbB-2, there were no positive cells in the normal lobules. The results are depicted in FIG. 3 and Table 8. In FIG. 3, the arrow points to the stained cells.

TABLE 8

Comparison of p53 an erbB-2 Immunostaining in Various Components of Breast Cancer Tissue

| | % Immunopositive In: | | |
|---|---|---|---|
| Case | Normal Adjacent | DCIS Component | Invasive Component |
| | p53 Immunopositive (%) | | |
| H12 | 0 | 1 | 1 |
| H40 | 0 | 10 | 10 |
| | erbB-2 Immunopositive (%) | | |
| H22 | 0 | 60 | 30 |
| H37 | 0 | 10 | 5 |
| H40 | 0 | 70 | 30 |

Although the foregoing invention has been described in detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed is:

1. A method for determining the likelihood of tissue in a human subject becoming malignant where the tissue is adjacent to breast carcinoma, comprising obtaining a sample of tissue adjacent to the carcinoma; determining a loss heterozygosity (LOH) at chromosome locus 3p2A in non-malignant tissue in the sample and correlating the LOH at chromosome locus 3p24 in non-malignant tissue in the sample with increased risk that the tissue in the human subject will become malignant.

2. The method according to claim 1, wherein the on-malignant tissue in the sample is benign hyperplastic tissue.

3. The method according to claim 1, wherein the non-malignant tissue in the sample is normal breast tissue.

4. The method according to claim 1, wherein the carcinoma is selected from the group consisting of interstitial in situ carcinoma, ductal in situ carcinoma and invasive carcinoma.

5. The method according to claim 1, further comprising the step of removing carcinoma tissue if present in the sample from non-malignant tissue in the sample prior to the determining of the LOH.

6. The method according to claim 1, comprising amplifying the 3p24 locus of chromosomal DNA in the sample.

7. The method according to claim 6, wherein the determining comprises analyzing the amplified DNA for a restriction fragment length polymorphism (RFLP) or tetranucleotide.

8. The method according to claim 7, wherein the analyzing comprises digesting the amplified DNA with a restriction nuclease selected from the group consisting of HindIII and MspI.

9. The method according to claim 1 further comprising the steps of isolating DNA from non-malignant tissue of the sample and annealing a nucleic acid to said sample DNA before determining the LOH of the sample, wherein said nucleic acid recognizes the 3p24 locus.

10. The method according to claim 9, wherein said nucleic acid is a primer for amplification of said sample DNA.

11. The method according to claim 9, further comprising amplifying the 3p24 locus of chromosomal DNA in the sample.

12. The method according to claim 10, wherein the primer for amplification is selected from the group consisting of SEQ ID NOS: 5 to 10.

13. The method according to claim 1, wherein the sample is immediately adjacent to the carcinoma.

14. The method according to claim 1, wherein the sample is from a lobule adjacent to the carcinoma.

* * * * *